United States Patent [19]

Hendrick et al.

[11] Patent Number: 4,855,667

[45] Date of Patent: Aug. 8, 1989

[54] PARALLEL PLATE DIELECTRIC ANALYZER

[75] Inventors: Kendall B. Hendrick, Landenberg, Pa.; John R. Reader, Jr., Newark, Del.

[73] Assignee: E. I. Du Pont de Nemours and Company, Wilmington, Del.

[21] Appl. No.: 206,092

[22] Filed: Jun. 13, 1988

[51] Int. Cl.[4] ............................................. G01R 27/26
[52] U.S. Cl. ................................ 324/61 R; 324/57 R; 324/61 P
[58] Field of Search ................. 324/57 R, 61 R, 61 P; 73/805, 790

[56] References Cited

U.S. PATENT DOCUMENTS

| | | | |
|---|---|---|---|
| 3,488,758 | 1/1970 | Benson et al. | 324/61 |
| 3,613,454 | 10/1971 | McFadin | 73/362 |
| 3,712,125 | 1/1973 | Meyer | 73/805 |
| 3,809,973 | 5/1974 | Hurley | 317/258 |
| 3,872,360 | 3/1975 | Sheard | 317/258 |
| 3,986,109 | 10/1976 | Poduje | 324/61 R |
| 4,082,906 | 4/1978 | Amin et al. | 428/539 |
| 4,096,758 | 6/1978 | Moore | 73/718 |
| 4,103,275 | 7/1978 | Diehl et al. | 338/25 |
| 4,129,848 | 12/1978 | Frank et al. | 338/308 |
| 4,140,998 | 2/1979 | Bettle | 340/199 |
| 4,186,368 | 1/1980 | White et al. | 338/28 |
| 4,387,339 | 6/1983 | Akerblom | 324/207 |
| 4,423,371 | 12/1983 | Senturia et al. | 324/61 R |
| 4,436,438 | 3/1984 | Voznick | 374/165 |
| 4,559,797 | 12/1985 | Raymond | 72/63 |
| 4,625,401 | 12/1986 | Cvijanovich | 29/885 |
| 4,678,991 | 7/1987 | Schmidt | 324/207 |
| 4,710,550 | 12/1987 | Kranbuehl | 526/60 |
| 4,723,908 | 2/1988 | Kranbuehl | 432/37 |

FOREIGN PATENT DOCUMENTS 2187291 9/1987 United Kingdom ............ 324/61 R

Primary Examiner—Reinhard J. Eisenzopf
Assistant Examiner—Anthony L. Miele
Attorney, Agent, or Firm—John M. Lynn

[57] ABSTRACT

A parallel plate dielectric analyzer is disclosed including: a distance sensor for accurately measuring the varying distance between the electrodes, such as a linear voltage differential transformer (LVDT), and a motor responsive to the distance sensor for positioning the electrodes; a force transducer for measuring the applied force on the sample and where the motor responsive to the distance sensor is also responsive to the force transducer to give a desired force by varying the electrode spacing; disposable electrodes made using thick film technology composed of a ceramic substrate with a conductor adhered to its surface; and a temperature sensor built into one of the electrodes such as a platinum ring adhered to the surface of one of the electrodes and means to measure the resistance across the platinum ring.

7 Claims, 5 Drawing Sheets

PARALLEL PLATE DIELECTRIC ANALYZER

BACKGROUND OF THE INVENTION

This invention relates to an apparatus for analyzing the dielectric properties of a sample by the use of parallel plate electrodes.

It is well known that by measuring the dielectric properties of a sample as a function of temperature, valuable information can be gained concerning the physical and chemical properties of the sample. For many years such measurements have been made by placing a sample between parallel plate electrodes, applying an electrical signal to one of the electrodes (i.e. the excitation electrode) and measuring the electrical signal from the other electrode (i.e. the response electrode) The following equation is used:

$$C = e_o e' A/d$$

where
- $C$ = Capacitance
- $e_o$ = Permitivity of Free Space (a constant)
- $e'$ = Permitivity of Sample (being measured)
- $A$ = Area of Parallel Plate Response Electrode
- $d$ = Distance Between the Excitation and Response Electrode Plates By measuring capacitance, the permitivity of the sample ($e'$) can easily be calculated if the area of the parallel plate electrode and the distance between the excitation and response electrodes are known. However, a common dilemma when making these measurements is obtaining an accurate measurement of distance between the plates. This is because most measurements are made as a function of temperature, and the sample changes in dimension as the experiment progresses. However, despite this fact, prior parallel plate dielectric analyzers have usually assumed the distance between the electrodes to be the thickness of the sample at room temperature. Thus, as the material expands or contracts as a function of temperature, the measured values are in error by the factor:

$$\frac{\text{Thickness of the Sample at Measurement Temperature}}{\text{Thickness of the Sample at Room Temperature}}$$

In some instances this error is compensated by allowing for the coefficient of thermal expansion (CTE) of the material (assuming it is known with some accuracy). But this is not an accurate correction since the CTE changes as a material goes through its glass transition. The CTE also assumes zero force on the sample which is not practical when making dielectric measurements on solid samples.

All known instruments either apply a constant force to a sample initially and run the experiment in that mode (constant force), or set a plate spacing and let it remain constant during an experiment (constant distance). In the constant force mode at elevated temperatures, when the sample melts, the two plates come together, short circuit, and the experiment is prematurely terminated. In the constant distance mode, if the sample melts, contact with the top plate is lost, and once again the experiment is prematurely terminated.

Another significant practical problem with conventional parallel plate dielectric analyzers arises because current analyzers use either steel or gold plated metallic plates. After a sample has passed its glass transition $T_G$ (point of interest), it begins to flow, and as it cools it can adhere to the highly-polished, precision-machined plates. Many times plates must be removed from the instrument to scrape samples off. The plates must then be reground to ensure parallelism for the next experiment. This can be a costly and time-consuming operation. One popular alternative is to use a thin release film (i.e. Teflon ®, a fluorocarbon polymer) to make sample removal easier. This film, however, influences the measurement of the dielectric properties and limits the experimental temperature to a temperature less than the melting point of the Teflon ® release film. (Ceramic sensors with a gold conductor are used in single plate dielectric analyzers. See; Micromet product literature in the Information Disclosure Statement—option S—60 dual function ceramic sensor for use in Micromet Eumetric System II microdielectrometer).

Accurate measurements of sample temperatures are also important since dielectric measurements are normally monitored as a function of temperature. In parallel plate dielectric analyzer, typically a thermocouple is placed as close to the edge of the sample and plate as possible without contact, and the sample temperature is assumed to be that of the thermocouple (melting a sample on the thermocouple would require extensive clean up or disposal of the thermocouple after the experiment). Obviously, this temperature measurement is not as accurate as measuring the temperature of the sample directly. (In single plate dielectric analyzers it is known to incorporate a thermal diode in the electrode. See; Micromet product literature in the Information Disclosure Statement - Option S-1 integrated circuit dielectric sensor for use in the Micromet Eumetric System II microdielectrometer).

A dielectric analyzer is needed which can vary the spacing between the electrodes as the sample expands, contracts or melts in order to keep the electrodes in constant contact with the sample. As the electrode spacing is varied, the analyzer must also be able to sense the distance between them so that the dielectric calculations are accurate regardless of electrode spacing. A dielectric analyzer is also needed which has electrodes which are easily replaced if their surfaces become marred. Lastly, a dielectric analyzer is needed which will give accurate temperature measurements of the sample.

SUMMARY OF THE INVENTION

Provided by this invention is an improved apparatus using parallel plate electrodes which measures the dielectric properties of a sample as a function of temperature having the following:

(a) a distance sensor for accurately measuring the varying distance between the electrodes, such as a linear voltage differential transformer (LVDT), and means responsive to the distance sensor for positioning the electrodes;

(b) a force transducer for measuring the applied force on the sample and means responsive to the force transducer to give a desired force by varying the electrode spacing;

(c) disposable electrodes made using thick film technology composed of a ceramic substrate with a conductor adhered to its surface; and (d) a temperature sensor built into one of the electrodes such as a metallic strip applied to the surface of one of the electrodes and means to measure the resistance across the metallic strip.

DETAILED DESCRIPTION

Figure 1:
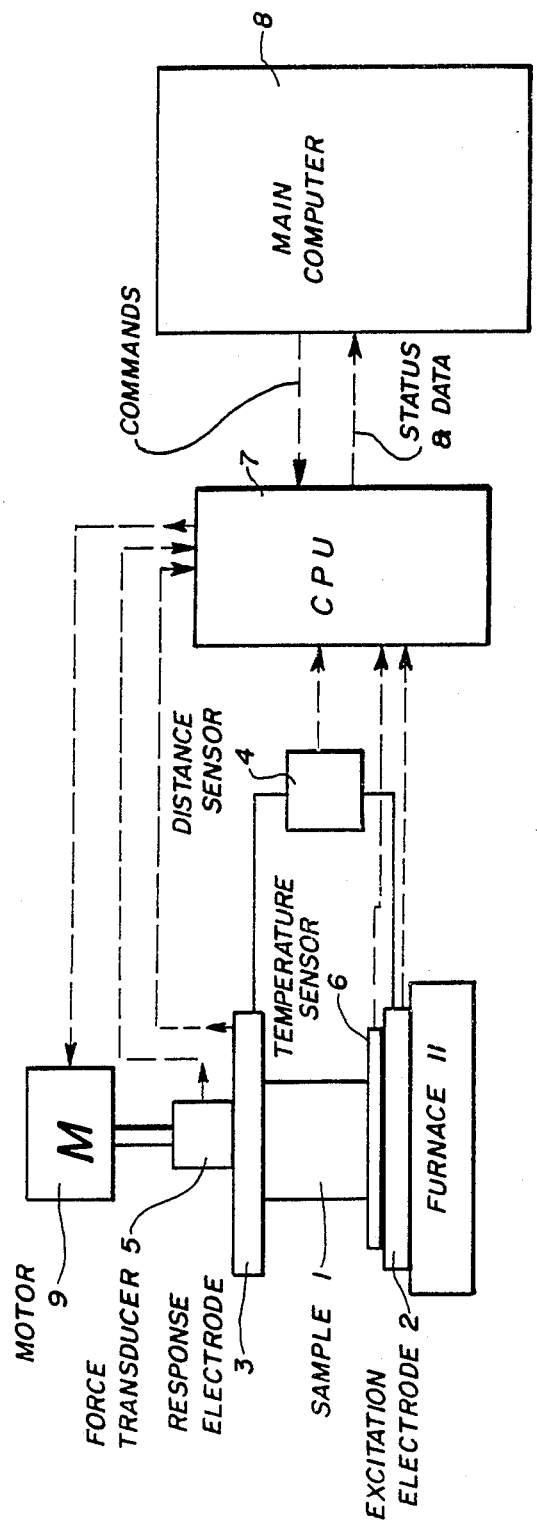
FIG. 1 is a schematic of the apparatus.

Referring now to the drawing in FIG. 1, the dielectric analyzer includes stationary excitation electrode 2 and moveable response electrode 3 positioned above excitation electrode 2. The electrodes are positioned parallel to each other and adapted to receive sample 1 there between. An electrical signal is provided to excitation electrode 2. The electrical signal passes through sample 1 and into response electrode 3. The output signal from electrode 3 is then sent to central processing unit (CPU) 7.

Excitation electrode 2 is in contact with heating unit 11. In order to calculate dielectric properties as a function of temperature, heating unit 11 is used to vary the sample temperature. A thermal method is programmed into computer 8 which gives commands to CPU 7 which in turn controls heating unit 11. The sample temperature is measured by temperature sensor 6 which is applied to excitation electrode 2. The signal from temperature sensor 6 is sent to CPU 7 for a temperature calculation and this data is then sent to computer 8 for data storage and further analysis.

As the temperature of the sample changes, the sample thickness varies as a function of its CTE. This can vary the distance between the electrodes. Because the calculation of the sample's dielectric properties is dependent upon knowing the correct distance between the electrodes, the apparatus includes distance sensor 4 to measure the distance between the electrodes. The distance sensor sends a signal to CPU 7. CPU 7 uses the signal to calculate the distance between the electrodes. CPU 7 then uses this distance calculation in conjunction with the input signal to excitation electrode 2, the output signal from response electrode 3 and the surface area of response electrode 3 to calculate the dielectric properties of the sample. This data on the sample's dielectric properties is then sent to computer 8 for storage and data analysis.

In addition, computer 8 can be programmed to command CPU 7 to vary the electrode spacing by using motor 9 to raise or lower response electrode 3. This feature is critical to ensure that if a sample melts, the electrodes don't come in contact with each other and prematurely terminate the experiment.

In order to assure that the electrodes are in constant contact with the sample, the apparatus includes force transducer 5 which measures the force exerted on the sample by response electrode 3. Force transducer 5 sends a signal to CPU 7 where the signal is processed to provide the force on the sample. This data is then fed to computer 8. Computer 8 can be programmed to command CPU 7 to give a desired force on the sample by raising or lowering response electrode 3 using motor 9.

Under normal operating conditions computer 8 is programmed to command CPU 7 to run under some minimal constant force in order to assure that the electrodes are in contact with the sample as its thickness varies as a function of temperature. However, computer 8 can also be programmed so that an override of the constant force mode occurs at some minimum electrode spacing. This will assure that if the sample melts, the electrodes don't come in contact with each other and short out.

Figure 2:
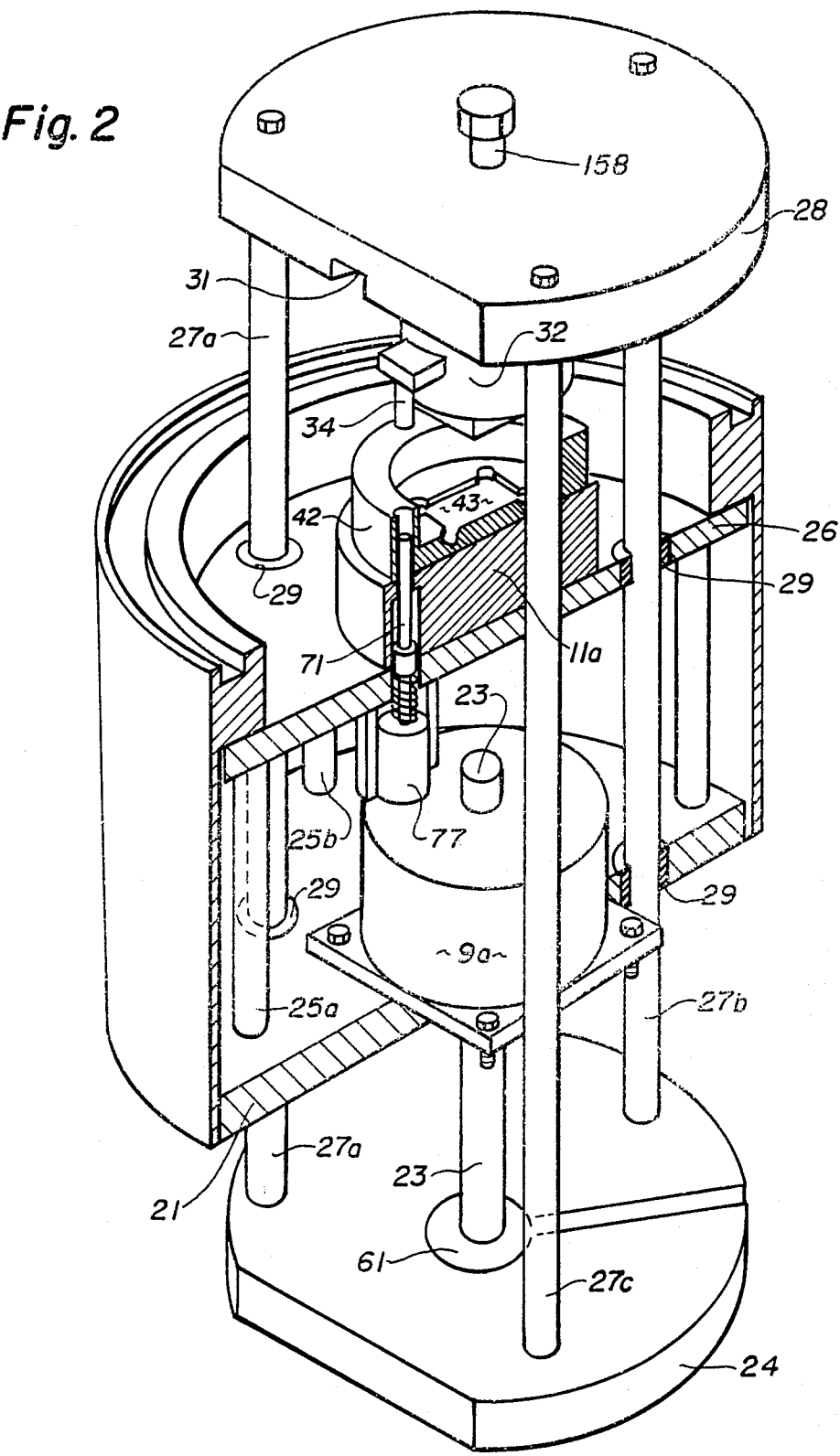
FIG. 2 is a perspective view of the apparatus with parts broken away to show the inside.

The preferred embodiment of the dielectric measurement apparatus is shown in FIG. 2. A disc shaped steel stationary base 21 lies in a horizontal plane and has three vertical steel columns 25a, 25b, and 25c of equal length attached to the upper surface of base 21. The columns are configured around the perimeter of base 21. The top of the steel columns are bolted to upper base 26 which is also a steel disc lying parallel to base 21.

Motor 9a is bolted to the upper surface of base 21. Positioned along the cylindrical axis of motor 9a is shaft 23 whose lower end is connected to plate 24, a steel disc. Numerous different types of motors can be used as will be apparent to one skilled in the art. In our preferred embodiment motor 9a is a permanent magnet stepping DC motor, EAD size 34, model number LA3-4AGK-9 manufactured by Eastern Air Devices. Plate 24 lies in a horizontal plane and has three vertical steel columns of equal length 27a, 27b and 27c bolted to its upper surface. The vertical steel columns pass through bearings 29 in base 21 and upper base 26. The top of columns 27a, 27b, and 27c are bolted to upper plate 28 which is a steel disc also lying in a parallel plane.

As motor 9a operates, shaft 23 moves up or down thereby moving plate 24 and upper plate 28 up or down.

Attached to the upper surface of upper base 26 is heating unit 11a. Heating unit 11a is used to heat the sample and consists of a furnace with accompanying support. As will be apparent to one skilled in the art, numerous different types of furnaces could be used. In our preferred embodiment the furnace is a mica clad inconel heater. Attached to and in contact with the upper surface of heating unit 11a is block 42 preferably brass, which serves as a platform for the excitation electrode. Block 42 is a bowl-shaped support which has an indentation 43 which is sized to hold the excitation electrode in place. (The instrument can also be used such that indentation 43 is used to hold an interdigitated single surface electrode.)

The bottom surface of upper plate 28 contains channel 31 fitted to slidably accept ram unit 32. Ram unit 32 is a ceramic housing designed to detachably hold response electrode 3a. Ram unit 32 also contains the electrical contacts for excitation electrode 2a, response electrode 3a, and the temperature sensor. Attached to the side of ram unit 32 and extending outwardly and then downwardly is vertical plunger 34. Ram unit 32 is discussed in more detail below.

Means to determine the distance between response electrode 3a and excitation electrode 2a is provided. Block 42, heating unit 11a and upper base 26 contain cavities sized and positioned such that linear voltage differential transformer (LVDT) 77 is placed directly beneath plunger 34. As ram unit 32 is lowered into position such that response electrode 3a is in contact with the sample, plunger 34 depresses spring loaded steel rod 71 which is attached to the core of LVDT 77. LVDT 77 operates in the same manner as LVDTs well known in the prior art. Spring loaded steel rod 71 is depressed by plunger 34 and the core moves through LVDT coil which is positionally fixed in relation to the moving core. This allows very precise and accurate determination of the distance between the response and excitation electrodes. The LVDT in our preferred embodiment is of the type TRANS TEK AC-AC #0291-0000 manufactured by Trans-Tek Inc.

Plate 24 includes force transducer 61. There are numerous types of force transducers known to one skilled in the art which will work in this application. In our preferred .embodiment the force transducer includes two steel blocks which clamp the ends of two solid state strain gauge force translators of the type Revere Model FT30-40. The other ends of both force sensors are clamped in a block which is rigidly fixed to the end of motor shaft 23. This arrangement allows precise and accurate measurement of the force motor 9a applies to plate 24. As ram unit 32 comes in contact with the sample, the force measured is equal to the force applied to the sample.

Figure 4:
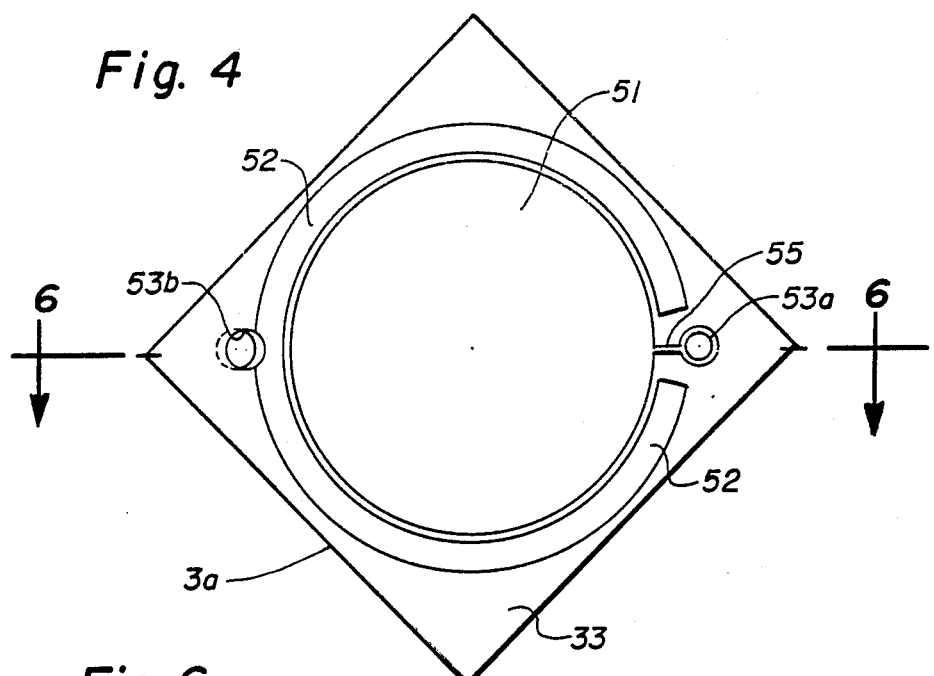
FIG. 4 is a bottom plan view of the response electrode as viewed from the line 4—4 of FIG. 3.
Figure 6:
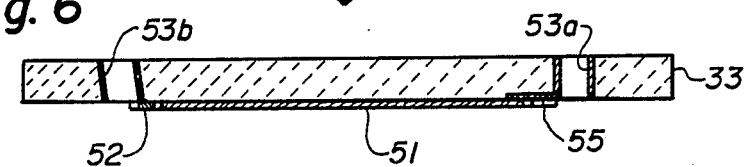
FIG. 6 is a sectional view of the response electrode taken on the line 6—6 of FIG. 4.

Detachably connected to the underside of ram unit 32 is response electrode 3a. Response electrode 3a (see FIGS. 4 and 6) comprises a thin square ceramic wafer substrate 33 with a thin round layer of gold conductor 51 applied to its surface. Guard ring 52 surrounds gold conductor 51. Guard ring 52 is a second thin circular, concentric layer of gold applied to ceramic substrate 33 which essentially surrounds but is not in contact with 51. (Guard rings are well known in the art and are used to assure that the signal received by the response electrode is unaffected by fringing fields.) Response electrode 3a has two gold plated holes 53a and 53b running completely through the ceramic wafer in opposing corners of the square. These gold plated holes are used as both electrical contacts and as receptors for mechanical grips used to hold response electrode 3a in place. Gold plated hole 53a is in electrical contact with gold conductor 51 through thin gold strip 55. Guard ring 52 is "broken" around gold strip 55 so that there is no electrical connection between gold conductor 51 and guard ring 52. Gold plated hole 53b intersects guard ring 52 and they, therefore, are also in electrical contact.

Figure 5:
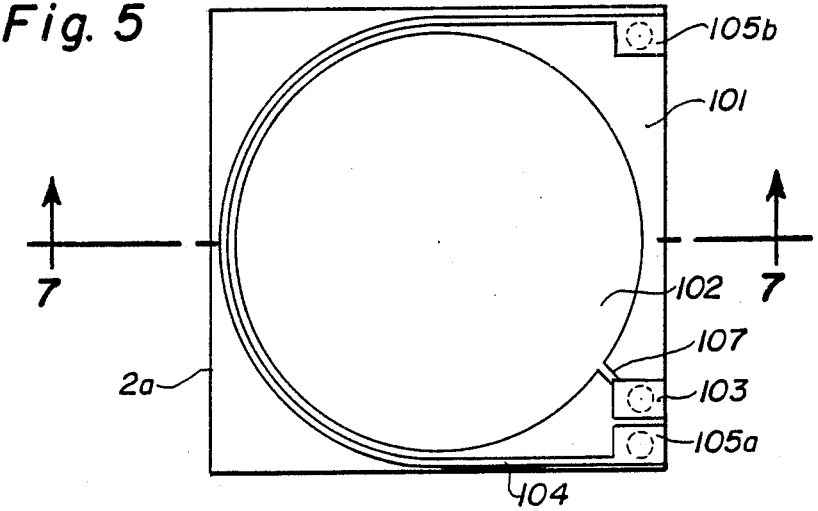
FIG. 5 is a top plan view of the excitation electrode as seen from the line 5—5 of FIG. 3.
Figure 7:
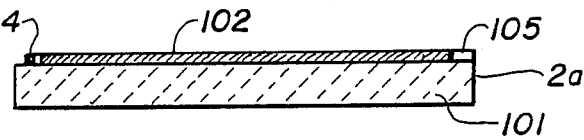
FIG. 7 is a sectional view of the excitation electrode take on the line 7—7 of FIG. 5.

Excitation electrode 2a (see FIGS. 5 and 7) is a thin square ceramic wafer 101 with a thin round gold layer 102 applied to its surface. Excitation electrode 2a sits in indentation 43 of block 42 with gold conductor 102 facing up. Thus, excitation electrode 2a is easily put into place or removed. Gold conductor 102 is in electrical contact with contact point 103 through gold strip 107. Also applied to the surface of ceramic wafer 101 is metallic strip 104, preferably platinum, running in a semicircle around the outside of gold conductor 102 but not in contact with gold conductor 102. At the end points of metallic strip 104 are electrical contact points 105a and 105b. Metallic strip 104 serves as a resistance temperature device. It is a well-known principal that by measuring the resistance of a metal, the temperature of the metal can be determined. Since metallic strip 104 is in direct contact with the sample, this gives a very accurate temperature reading of the sample.

Both the excitation and response electrodes are manufactured using thick film hybrid technology (screen printed conductor layers) well known to those skilled in the art.

Figure 3:
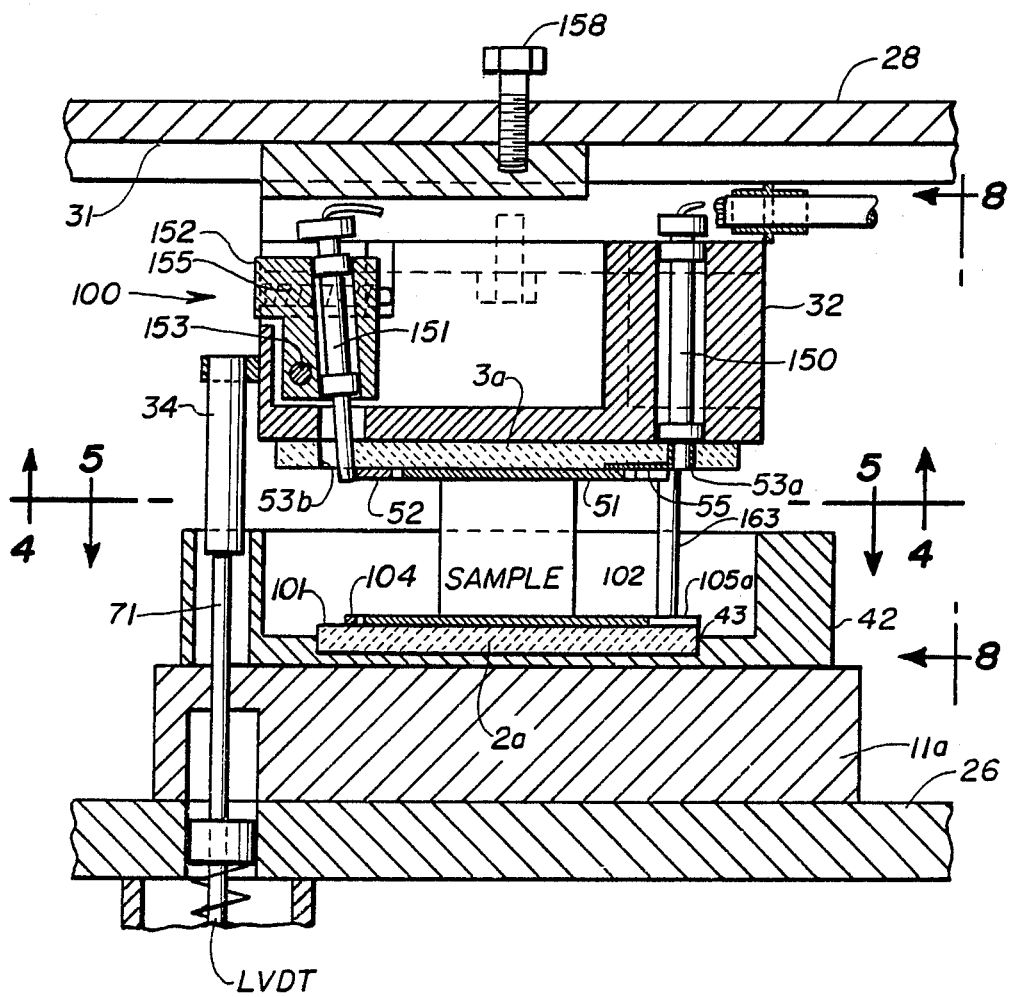
FIG. 3 is an enlarged fragmentary vertical sectional view of the ram unit of the apparatus.

FIG. 3 shows a cross section of upper plate 26, ram unit 32, response electrode 3a, sample 1, excitation electrode 2a, block 42, furnace 11a and upper base 26. Response electrode 2a is seated in indentation 43 of block 42. The sample is placed on the upper surface of excitation electrode 2a. Response electrode 3a is in contact with the upper surface of the sample and is detachably attached to ram unit 32.

Attachment and detachment of response electrode 3a to ram unit 32 is accomplished using stationery pin 150 and movable pin 151. These pins serve as both mechanical grips and electrical contacts. The pins are sized and spaced such that they fit into gold plated holes 53a and 53b of response electrode 3a. Pin 150 goes in hole 53a and pin 151 goes in hole 53b. Stationery pin 150 is seated in a cavity in ram unit 32. Moveable pin 151 is seated in rotating housing 152 which is pivotally attached to ram unit 32 by means of pivot screws 153. Only one of the pivot screws is visible in FIG. 3. Rotating housing 152 contains spring pin 155 applying a counterclockwise force to the rotating housing around pivot screws 153. This in turn exerts a counterclockwise force on pin 151 which grips the interior surface of hole 53b and holds response electrode 3a into place. To release response electrode 3a, pressure is exerted on the upper exposed portion of rotating housing 152 as shown by arrow 100. This counteracts the force exerted by spring pin 155, and causes rotating housing 152 and pin 151 to rotate clockwise. This rotation of pin 151 allows response electrode 3a to be slipped off of pin 150 and pin 151.

Figure 8:
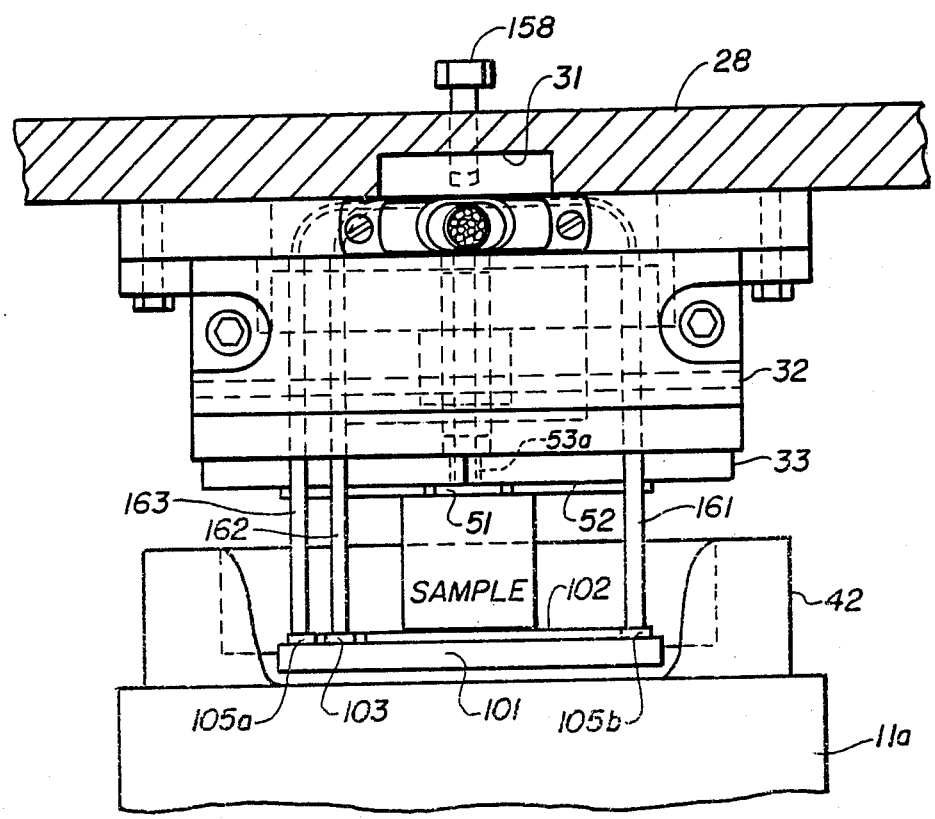
FIG. 8 is a fragmentary elevational view of the apparatus of FIG. 3 as seen from the plane 8—8 of FIG. 3 and with the proximate wall of block 42 broken away to better show the structure there behind.

Excitation electrode 2a (shown in FIGS. 5 and 7) sits in indentation 43 of block 42. The electrical signals needed to excite conductor 102 and measure the resistance across platinum strip 104 are received from electrical pogo pins 161, 162, and 163 as shown in FIG. 8. Only pin 163 is visible in FIG. 3. These pins are common spring loaded electrical pogo pins which are seated in the ceramic housing of ram unit 32. Pins 161, 162 and 163 are positioned so that as ram unit 32 is lowered the pins contact their respective electrical contact points 105a, 105b and 103 on the surface of excitation electrode 2a. Pin 161 is in contact with electrical contact point 105b, pin 162 is in contact with electrical contact point 103 and pin 163 is in contact with electrical contact point 105a.

Operation of the Apparatus

Initially ram unit 32 is decoupled from the instrument. The response electrode is attached to ram unit 32 by slipping pins 150 and 151 through holes 53a and 53b when rotating housing 152 is pressured such that it has rotated clockwise (as shown in FIG. 3). Releasing the spring loaded rotating housing 152 "grips" response electrode 3a and holds it in place with gold conductor 51 facing down. Ram unit 32 is then affixed to upper plate 28 by sliding ram unit 32 into channel 31. Ram unit 32 is then captured rigidly by tightening thumbscrew 158. Excitation electrode 2a is placed in indentation 43 in block 42 with gold conductor 102 and platinum RTD 104 facing up.

At this point, calibration is begun. Motor 9a begins to drive, bringing ram unit 32 toward excitation electrode 2a. Pogo pins 161, 162 and 163 make electrical connection with electrical contact points 105b, 103, and 105a, respectively. Motor 9a continues to drive until electrodes 2a and 3a are in contact with each other. LVDT calibration is set to 0.0 millimeters at this point. Motor 22 reverses direction and ram unit 32 travels upward to remove all mechanical backlash from the system. An LVDT reading is taken at this point then ram unit 32 travels upward again as a predetermined number of motor steps are being counted. Another LVDT calibration reading is then taken. By knowing the pitch of the motor lead screw and the number of steps driven, the theoretical distance traveled can be calculated. A two point calibration of the LVDT has been completed and stored in computer 8.

Knowing the gain of the LVDT, motor 9a drives ram unit 32 down to a selected distance between the electrodes. Now a sinusoidal voltage is applied to excitation electrode 2a. The resulting current is monitored at response electrode 3a. Knowing the dielectric properties of dry air, the electrodes are calibrated for dielectric measurements. Concurrently, the resistance of platinum strip 104 is being measured and calibrated. (Knowing the temperature of the furnace block via a thermocouple embedded within it, the RTD is calibrated to the thermocouple temperature). After all calibration values are stored, ram unit 32 moves to full open position. A sample of interest is then placed on the excitation electrode 2a. A constant force or spacing experiment is selected. Threshold values (minimum/maximum) are determined and programmed into computer 8. A thermal method is programmed into computer 8. The experiment is ready to begin.

Ram unit 32 then moves to the selected force or spacing and begins measuring the capacitance of the sample concurrent with the thermal method of heating unit 11a. As the experiment progresses, computer 8 dynamically monitors force and spacing and drives motor 9a accordingly to maintain operator selected parameters.

By measuring capacitance, the permitivity of the sample (e') can easily be calculated using the following equation:

$$C = e_0 e' A/d$$

where
C = Capacitance
$e_0$ = Permitivity of Free Space (a constant)
e' = Permitivity of Sample (being measured)
A = Area of Parallel Plate Response Electrode
d = Distance Between the Excitation and Response Electrode Plates

We claim:

1. In an apparatus for measuring the dielectric properties of a sample, the apparatus including an excitation electrode and a response electrode adapted to receive the sample there between, the electrodes being positionable to adjust the distance there between, a temperature sensor adapted to sense the temperature of the sample, means for applying an input electrical signal to the excitation electrode, and means connected to the response electrode for providing an output signal; wherein the input electrical signal to the excitation electrode passes through the sample into the response electrode and becomes the output electrical signal, such that by measuring the input electrical signal and the output electrical signal the dielectric properties of the sample can be calculated by knowing the distance between the electrodes and the response electrode surface area, the improvement which comprises:
   (a) a distance sensor for measuring the distance between the electrodes, and means responsive to the distance sensor for positioning the electrodes relative to each other;
   (b) a force transducer for measuring applied force on said sample where said means responsive to said distance sensor are also responsive to said force transducer for varying the spacing between electrodes;
   (c) said electrodes are comprised of a ceramic substrate with a conductor applied to the ceramic substrate;
   (d) said temperature sensor comprising a metallic strip applied to one of the electrodes and means to measure the resistance across said metallic strip.

2. The apparatus of claim 1 wherein the distance sensor is a linear voltage differential transformer.

3. The apparatus of claim 2 wherein the force transducer is an active full bridge strain gauge.

4. The apparatus of claim 3 wherein the means responsive to the force transducer to give a desired force by varying the electrode spacing comprises:
   (a) a central processing unit;
   (b) a computer; and
   (c) a motor
wherein the force transducer sends a signal to the central processing unit for processing and comparison with said desired force, the central processing unit commands the motor to vary the electrode spacing accordingly, and sends the processed data to the computer for storage.

5. The apparatus of claim 4 where the means responsive to the distance sensor for positioning the electrode comprises
   (a) said central processing unit;
   (b) said main computer; and
   (c) said motor
wherein the distance sensor sends a signal to the central processing unit for processing and comparison with a desired electrode spacing, the central processing unit then commands the motor to vary the electrode spacing accordingly, and sends the processed data to the computer for storage.

6. The apparatus of claim 5 wherein the computer is programmed for closed loop control over the electrode spacing and force.

7. In an apparatus for measuring the dielectric properties of a sample, the apparatus including an excitation electrode and a response electrode adapted to receive the sample there between, the electrodes being positionable to adjust the distance there between, a temperature sensor adapted to sense the temperature of the sample, means for applying an input electrical signal to the excitation electrode, and means connected to the response electrode for providing an output signal; wherein the input electrical signal to the excitation electrode passes through the sample into the response electrode and becomes the output electrical signal, such that by measuring the input electrical signal and the output electrical signal the dielectric properties of the sample can be calculated by knowing the distance between the electrodes and the response electrode surface area, the improvement which comprises:
   (a) a distance sensor for measuring the distance between the electrodes, and means responsive to the distance sensor for positioning the electrodes relative to each other;
   (b) a force transducer for measuring applied force on said sample where said means responsive to said distance sensor are also responsive to said force transducer for varying the spacing between electrodes; and
   (c) at least one of said electrodes is comprised of a ceramic substrate.

* * * * *